(12) United States Patent
Valdez et al.

(10) Patent No.: US 10,082,514 B2
(45) Date of Patent: *Sep. 25, 2018

(54) METHODS FOR THE SELECTIVE DETECTION OF ALKYNE-PRESENTING MOLECULES AND RELATED COMPOSITIONS AND SYSTEMS

(71) Applicant: LAWRENCE LIVERMORE NATIONAL SECURITY, LLC, Livermore, CA (US)

(72) Inventors: Carlos A. Valdez, San Ramon, CA (US); Audrey M. Williams, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 913 days.

This patent is subject to a terminal disclaimer.

(21) Appl. No.: 14/201,480

(22) Filed: Mar. 7, 2014

(65) Prior Publication Data

US 2014/0273250 A1 Sep. 18, 2014

Related U.S. Application Data

(60) Provisional application No. 61/790,393, filed on Mar. 15, 2013, provisional application No. 61/790,019, filed on Mar. 15, 2013, provisional application No. 61/790,757, filed on Mar. 15, 2013.

(51) Int. Cl.
| | | |
|---|---|---|
| *G01N 33/74* | (2006.01) | |
| *G01N 33/53* | (2006.01) | |
| *C08F 112/08* | (2006.01) | |
| *G01N 33/18* | (2006.01) | |
| *G01N 33/00* | (2006.01) | |

(52) U.S. Cl.
CPC .......... *G01N 33/743* (2013.01); *C08F 112/08* (2013.01); *G01N 33/1826* (2013.01); *G01N 33/5308* (2013.01)

(58) Field of Classification Search
CPC ............. G01N 33/743; G01N 33/5308; G01N 33/1826; C08F 112/08
USPC ........................ 436/71; 546/304, 332; 552/4
See application file for complete search history.

(56) References Cited

U.S. PATENT DOCUMENTS

| | | | |
|---|---|---|---|
| 2008/0241856 A1* | 10/2008 | Wong ................ | G01N 1/30 435/7.1 |
| 2009/0297609 A1 | 12/2009 | Shoichet et al. | |
| 2012/0226019 A1 | 9/2012 | Aucagne et al. | |
| 2014/0273274 A1 | 9/2014 | Valdez et al. | |
| 2014/0275432 A1 | 9/2014 | Valdez et al. | |

FOREIGN PATENT DOCUMENTS

GB     1325912 A     8/1973

OTHER PUBLICATIONS

Restriction Requirement for U.S. Appl. No. 14/201,545, filed Mar. 7, 2014 on behalf of Carlos A. Valdez. Dated: Oct. 7, 2015. 7 pages.

(Continued)

*Primary Examiner* — Rebecca M Fritchman
(74) *Attorney, Agent, or Firm* — Steinfl + Bruno, LLP

(57) ABSTRACT

Provided herein are methods for selectively detecting an alkyne-presenting molecule in a sample and related detection reagents, compositions, methods and systems.

10 Claims, 11 Drawing Sheets

(56) References Cited

OTHER PUBLICATIONS

Non-Final Office Action for U.S. Appl. No. 14/201,545, filed Mar. 7, 2014 on behalf of Carlos A. Valdez. Dated: Dec. 17, 2015. 13 pages.
Final Office Action for U.S. Appl. No. 14/201,545, filed Mar. 7, 2014 on behalf of Carlos A. Valdez. Dated: Jul. 14, 2016. 14 pages.
Restriction Requirement for U.S. Appl. No. 14/201,480, filed Mar. 7, 2014 on behalf of Carlos A. Valdez. Dated: Sep. 9, 2016. 10 pages.
Balli et al. "Synthese von 1-Athyl-2-azido-6-X-chinolinium-fluoroboraten" Helvetica Chimica Acta; 1970; vol. 53; No. 7; pp. 1903-1912—English Abstract Only + Full German text.
Sezer et al. "Transdiazotization of Acylacetaldehydes in Neutral-to-Acidic Medium. A Direct Approach to the Synthesis of α-Diazo-β-oxoaldehydes')" Helvetica Chimica Acta; 1994; vol. 77; pp. 2323-2334.
Szanti-Pinter et al. "Synthesis of ferrocene-labelled steroid derivatives via homogenous catalytic methods" Journal of Organometallic Chemistry; 2012; vol. 718; pp. 105-107.
Szanti-Pinter et al. "Synthesis of steroid-ferrocene conjugates of steroidal 17-carboxamides via a palladium-catalyzed aminocarbonylation—Copper-catalyzed azide-alkyne cycloaddition reaction sequence" Steroids; 2011; vol. 76; pp. 1377-1382.
Upton et al. "Synthesis of ferrocene-functionalized monomers for biodegradable polymer formation" Inorg. Chem. Front.; 2014; vol. 1; pp. 271-277.
Sletten, E.M. and Bertozzi, C.R. "Bioorthogonal chemistry: fishing for selectivity in a sea of functionality" *Angew Chem Int Ed Engl* (2009) 48, 38, pp. 6974-6998.
Prescher, J.A., et al., "Chemical remodeling of cell surfaces in living animals." *Nature* (2004) vol. 430, pp. 873-877.
Sawa, M., et al., "Glycoproteomic probes for fluorescent imaging of fucosylated glycans in vivo." *Proc Natl Acad Sci USA* (2006) vol. 103, 33, pp. 12371-12376.
Baskin, J.M., et al., "Copper-free click chemistry for dynamic in vivo imaging" *Proc Natl Acad Sci USA* (2007) 104, 43, pp. 16793-16797.
Zhang, L., et al., "Ruthenium-catalyzed cycloaddition of alkynes and organic azides" *J Am Chem Soc* (2005) vol. 27, 46, pp. 15998-15999.
Horiba, J.Y., "A Guide to Recording Fluorescence Quantum Yields" (2002), 6 pgs.
Trupp, S. et al., "A fluorescent water-soluble naphthalimide-based receptor for saccharides with highest sensitivity in the physiological pH range." *Org. Biomol. Chem.* (2006) vol. 4, pp. 2965-2968.
Schneider, C. et al., "Direct sub-ppt detection of the endocrine disruptor ethinylestradiol in water with a chemiluminescence enzyme-linked immunosorbent assay." *Anal. Chim. Acta* (2005) vol. 551, pp. 92-97.
Sivakumar, K. et al., "A Fluorogenic 1,3-Dipolar Cycloaddition Reaction of 3-Azidocoumarins and Acetylenes" *Org. Lett.* (2004) vol. 6, pp. 4603-4606.
Rostovtsev, V. V. et al., "A Stepwise Huisgen Cycloaddition Process: Copper(I)-Catalyzed Regioselective "Ligation" of Azides and terminal alkynes." *Angew. Chem. Int. Ed. Engl.* (2002) vol. 41, pp. 2596-2599.
Tornoe, C. et al., "Peptidotriazoles on Solid Phase: [1,2,3]-triazoles by Regiospecific Copper(I)—Catalyzed 1,3-Dipolar Cycloadditions of Terminal Alkynes to Azides" *J. Org. Chem.* (2002) vol. 67, pp. 3057-3064.
Fery-Forgues, S. et al., "Are Fluorescence Quantum Yields So Tricky to Measure? A Demonstration Using Familiar Stationery Products" *J. Chem. Ed.* (1999) vol. 76, pp. 1260-1264.
Snyder, S. A. et al., "Analytical Methods for Detection of Selected Estrogenic Compounds in Aqueous Mixtures" *Environ. Sci. Technol.* (1999) vol. 33, pp. 2814-2820.
Colborn, T. "Building Scientific Consensus on Endocrine Disruptors" *Environmental Toxicology and Chemistry* (1998) vol. 17(1), pp. 1-2.
Smith, P. A. S. and Hall, J.H. "Kinetic Evidence for the Formation of Azene (Electron-Deficient Nitrogen) Intermediates from Aryl Azides" *J. Am. Chem. Soc.* (1961) vol. 84, pp. 480-485.
Melhuish, W. H. "Quantum Efficiencies of Fluorescence Organic Substances: Effect of Solvent and Concentration of the Fluorescent Solute" *J. Phys. Chem.* (1960) vol. 65, pp. 229-235.
Richardson, S.D., "Water Analysis: Emerging Contaminants and Current Issues" *Anal. Chem.* (2009) vol. 81, pp. 4645-4677.
Hanaoka, K., et al., "Design and Synthesis of a Highly Sensitive Off-On Fluorescent Chemosensor for Zinc Ions Utilizing Internal Charge Transfer" *Chem. Eur. J.* (2010), vol. 16, pp. 568-572.
Martinez, N.A. et al., "Modified Paramagnetic Beads in a Microfluidic System for the Determination of Ethinylestradiol (EE2) in River Water Samples" *Biosensors and Bioelectronics,* vol. 25 (2010), pp. 1376-1381.
Hannah, R., et al., "Exposure Assessment of 17α-Ethinylestradiol in Surface Waters of the United States and Europe" *Environmental Toxicology and Chemistry* (2009) vol. 28(12), pp. 2725-2732.
Van Berkel, G.J., et al. "Deprivation for Electrospray Ionization Mass Spectrometry. 3. Electrochemically Ionizable Derivatives." Anal. Chem., vol. 70, pp. 1544-1554. 1998.
Higashi, T. et al. "Derivatization of neutral steroids to enhance their detection characteristics in liquid chromatography-mass spectrometry." Anal Bioanal Chem., vol. 378, pp. 872-882. 2004.
Ternes, T.A. et al. "Determination of Estrogens in Sludge and Sediments by Liquid Extraction and GC/MS/MS." Anal. Chem., vol. 74, pp. 3498-3504. 2002.
Thompson, A. S. et al. "Direct Conversion of Activated Alcohols to Azides Using Diphenyl Phosphorazidate. A Practical Alternative to Mitsunobu Conditions." J. Org. Chem., vol. 58, pp. 5886-5888. 1993.
Cassidy, M.P. et al. "Practical Synthesis of Amides from In Situ Generated Copper (I) Acetylides and Sulfonyl Azides." Angew. Chem. Int. Ed., vol. 45, pp. 3154-3157. 2006.
Danheiser, R.L. et al. "An Improved Method for the Synthesis of a α-Diazo Ketones." J. Org. Chem., vol. 55(6), pp. 1959-1964. 1990.
Shved, N. et al. "Environmentally Relevant Concentrations of 17α-Ethinylestradiol (EE2) Interfere With the Growth Hormone (GH)/Insulin-Like Growth Factor (IGF)—I Systems in Developing Bony Fish." Toxicological Science, vol. 106(1), pp. 93-102. 2008.
Seiwert, B. and Karst, U. "Ferrocene-based derivatization in analytical chemistry." Anal Bioanal Chem., vol. 390, pp. 181-200. 2008.
Fukuzawa, S. et al. "ClickFerrophos: New Chiral Ferrocenyl Phosphine Ligands Synthesized by Click Chemistry and the Use of Their Metal Complexes as Catalysts for Asymmetric Hyrdogenation and Allylic Substitution." Organic Letter, vol. 9(26), pp. 5557-5560. 2007.
Quirke, J.M.E. et al. "Ferrocene-Based Electroactive Derivatizing Reagents for the Rapid Selective Screening of Alcohols and Phenols in Natural Product Mixtures Using Electrospray—Tandem Mass Spectrometry." J. Nat. Prod., vol. 63, pp. 230-237. 2000.
Kuch, H. M. et al. "Determination of Endocrine-Disrupting Phenolic Compounds and Estrogens in Surface and Drinking Water by HRGC-(NCI)-MS in the Picogram per Liter Range." Environ. Sci. Technol. vol. 35, pp. 3201-3206. 2001.
Barnett, S.M. et al. Surface-Enhanced Raman Scattering Spectroscopic Study of 17α Ethinylestradiol on Silver Colloid and in Glass-Deposited Ag—I 7a-Ethinylestradiol Film. Anal.Chem., vol. 66, pp. 1762-1765. 1994.
Van Berkel, G.J. et al. "Preforming Ions in Solution via Charge-Transfer Complexation for Analysis by Electrospray Ionization Mass Spectrometry." Anal. Chem., vol. 63 (18), pp. 2064-2068. 1991.
Restriction Requirement for U.S. Appl. No. 14/201,530, filed Mar. 7, 2014 on behalf of Carlos A. Valdez. Dated: Sep. 1, 2016. 10 pages.
Non-Final Office Action for U.S. Appl. No. 14/201,530, filed Mar. 7, 2014 on behalf of Carlos A. Valdez. Dated: Jan. 25, 2017. 19 pages.
Non-Final Office Action for U.S. Appl. No. 14/201,545, filed Mar. 7, 2014 on behalf of Carlos A. Valdez. Dated: Apr. 6, 2017. 13 pages.

(56) References Cited

OTHER PUBLICATIONS

Sigma-Aldrich, Excerpt from "Resins for Solid-Phase Synthesis" retrieved from http://web.archive.org/web/20120629084629/http://www.sigmaaldrich.com/chemistry/drug-discovery/resin-explorer/solid-phase-resins.html on Jan. 12, 2017. 1 page.
7 Fluka, Resins for solid-phase Peptide Synthesis, vol. 3, No. 4, 2003, 32 pages.
Tian, H. et al. "Micelle-induced multiple performance improvement of fluorescent probes for H2S detection" Analytica Chimica Acta, 2013, vol. 768, pp. 136-142.
Final Office issued for U.S. Appl. No. 14/201,480, filed Mar. 7, 2014 on behalf of Carlos A. Valdez. Dated: Dec. 29, 2017. 8 pages.
Notice of Allowance for U.S. Appl. No. 14/201,530, filed Mar. 7, 2014 on behalf of Carlos A. Valdez et al. Dated: Jun. 28, 2017. 9 pages.
Field et al., "Alkylbenzenesulfonates and Dialkyltetralinsulfonates in Sewage-Contaminated Groundwater", Environ. Sci. Technol. ,1992, vol. 26, pp. 1140-1148.

* cited by examiner

METHODS FOR THE SELECTIVE DETECTION OF ALKYNE-PRESENTING MOLECULES AND RELATED COMPOSITIONS AND SYSTEMS

CROSS REFERENCE TO RELATED APPLICATIONS

The present application claims priority to U.S. Provisional Application 61/790,393 entitled "Methods for The Selective Detection of Alkyne-Presenting Molecules and Related Compositions and Systems" filed on Mar. 15, 2013, to U.S. Provisional Application 61/790,019 entitled "Methods for The Selective Detection of Alkyne-Presenting Molecules and Related Compositions and Systems" filed on Mar. 15, 2013, and to U.S. Provisional Application 61/790,757 entitled "Methods for The Selective Sequestration of Alkyne-Presenting Molecules and Related Compositions and Systems" filed on Mar. 15, 2013, each of which is herein incorporated by reference in their entirety. This application may be related to U.S. Non-Provisional application Ser. No. 14/201,530 and entitled "Methods for The Selective Detection of Alkyne-Presenting Molecules and Related Compositions and Systems" filed on Mar. 7, 2014 and to U.S. Non-Provisional application Ser. No. 14/201,545 and entitled "Methods for The Selective Sequestration of Alkyne-Presenting Molecules and Related Compositions and Systems" filed on Mar. 7, 2014, each of which is herein incorporated by reference in their entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to methods for detection of alkyne-presenting molecules, and in particular 17α-ethinylestradiol, and related compositions and systems.

BACKGROUND

Detection of alkyne-presenting molecules, such as 17α-ethinylestradiol and other steroid-based contaminants, in the environment, particularly in water systems, has become an issue of utmost importance due to the toxic effects exerted by these chemical species in biological systems even at very low concentrations.

However, specific and selective detection of those compounds can be challenging also in view of the fact that several synthetic and natural chemicals possess the ability to mimic hormones and as such are able to interfere or disrupt hormonal homeostasis in biological systems.

Accordingly, despite the fact that several methods and systems for detection of alkyne-presenting molecules, and in particular 17α-ethinylestradiol, are available, performance of an accurate and selective detection remains challenging.

SUMMARY

Described herein are methods and related compositions and systems that in some embodiments can be used in the selective detection and quantification of steroids, and in particular, the selective detection and quantification of alkyne presenting molecules, and in particular 17α-ethinylestradiol.

According to a first aspect, a method and system for selectively detecting alkyne-presenting molecules, and in particular 17α-ethinylestradiol, in an unprepared sample is described, the method comprising: contacting a detection reagent with the unprepared sample for a time and under a condition to allow binding of one or more alkyne-presenting molecules possibly present in the sample to the detection reagent wherein the detection reagent comprises an organic or organometallic label moiety presenting an azide or sulfonyl azide group wherein binding of detection reagent to one or more alkyne presenting molecule comprises binding of the azide group to an alkyne group of the alkyne-presenting molecules and wherein binding of the azide or sulfonyl azide group to the alkyne-presenting molecule results in emission of a signal from the organic or organometallic label moiety. In some embodiments, the organic or organometallic label moiety can comprise a positively charged moiety. In other embodiments, the organic or organometallic label moiety can comprise a ferrocenyl moiety. The system comprises at least one of one or more detection reagents herein described, reagents for the alkyne group azide group reaction and/or a copper(I) source for the simultaneous, combined, or sequential use in the method herein described.

According to a second aspect, a detection reagent is described, the detection reagent comprising: one or more label organic or organometallic moieties, the label organic or organometallic moieties each presenting an azide or sulfonyl azide group; wherein the label organic or organometallic moieties are adapted to produce a signal when the detection reagent is bound to one or more alkyne-presenting molecules, and in particular 17α-ethinylestradiol molecules. In some embodiments, the signaling moieties are positively charged moieties. In other embodiments, the signaling moieties are ferrocenyl moieties. In some embodiments, the binding moieties are azide groups. In other embodiments, the binding moieties are sulfonyl azide groups.

The methods and related compositions and systems described herein in several embodiments allow the selective detection by mass spectrometry of alkyne-presenting molecules, and in particular 17α-ethinylestradiol, in unprepared aqueous and organic samples.

The methods and related compositions and systems described herein in several embodiments can be used, for example, for the detection and analysis of the alkyne-presenting molecules, such as contraceptive pill's active ingredient 17-α-ethinylestradiol (EE2), in various unprepared water matrices and organic media using the technique of mass spectrometry. Furthermore, application of these methods and related compositions and systems can be extended, for example, to EE2 detection in blood and urine samples that can become important if monitoring systems are to be developed for individuals consuming the drug.

The methods and related compositions and systems described herein in several embodiments can be used, for example, for the detection and/or removal of the contraceptive pill's active ingredient 17-α-ethinylestradiol (EE2) from various water matrices and organic media using the Cu(I)-catalyzed 1,3-dipolar cycloaddition reaction commonly known as "click chemistry". Furthermore, application of these methods and related compositions and systems can be extended to the building of purification devices that possess the azido-functionality and thus are able to directly interact with alkyne-presenting molecules such as EE2 without the need for sample preparation.

The details of one or more embodiments of the disclosure are set forth in the accompanying drawings and the description below. Other features and objects will be apparent to a skilled person from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 4A shows and exemplary synthesis of ferrocenyl isocyanate via a Curtius rearrangement. FIG. 4B shows an exemplary reaction between ferrocenyl isocyanate and Campesterol to yield a ferrocene-tagged molecule that is readily detectable by ESI-MS [Ref 1].

DETAILED DESCRIPTION

Figure 1:
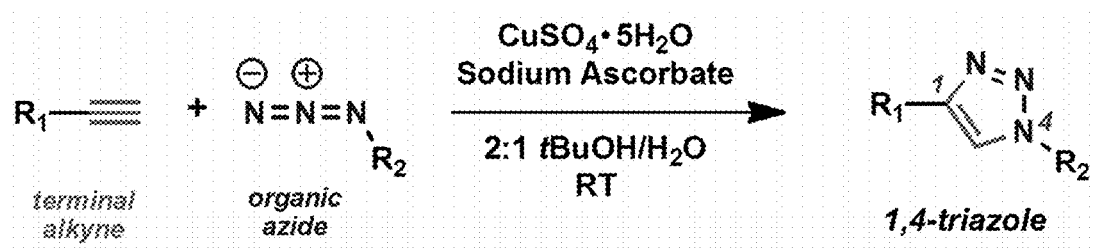
FIG. 1 shows a schematic of The Cu(I)-catalyzed Azide-Alkyne Dipolar Cycloaddition reaction (Click chemistry). Note that the product is a 1,4-substituted triazole ring joining species $R_1$ and $R_2$.

Described herein are methods and related compositions and systems that in some embodiments can be used in the selective detection and/or quantification of alkyne-presenting molecules, and in particular, the selective detection and or quantification of alkyne presenting molecule, and in particular 17α-ethinylestradiol.

The term "alkyne presenting molecule" as used herein indicates a molecule presenting a alkyne group for binding. The term "present" as used herein with reference to a compound or functional group indicates attachment performed to maintain the chemical reactivity of the compound or functional group as attached. Accordingly, an alkyne group presented on a molecule, is able to perform under the appropriate conditions the one or more chemical reactions that chemically characterize the alkyne group including click chemistry. In particular, an alkyne group can be included in an alkyne presenting molecule in any position and configuration as long as the alkyne group is presented in the molecule for binding or be subjected to other reactions.

In some embodiments herein described, the alkyne presenting molecule comprises a terminal alkyne. Exemplary molecule wherein the alkyne presenting molecule comprises a terminal alkyne include, for example, 17α-ethinylestradiol, acetylene, propyne, norethynodrel, rasagiline, and others identifiable to a skilled person.

In some embodiments herein described the alkyne presenting molecule comprises an internal alkyne group. Exemplary molecule wherein the alkyne presenting molecule comprises an internal alkyne include, for example, terbinafine, cicutoxin, oenanthotoxin, falcarinol, efavirenz, calicheamicin, tariric acid, and others identifiable to a skilled person.

In particular, in some embodiments, the methods and related compositions and systems can be used in the selective detection of alkyne-presenting molecules, and in particular 17α-ethinylestradiol in unprepared aqueous and organic samples.

The terms "detect" or "detection"; as used herein indicates the determination of the existence, presence or fact of a target in a limited portion of space, including but not limited to a sample, a reaction mixture, or other limited portion of space identifiable to a skilled person upon a reading of the present disclosure. The detection can be quantitative or qualitative. A detection is "quantitative" when it refers to, relates to, or involves the measurement of quantity or amount of the target or signal (also referred as quantitation), which includes but is not limited to any analysis designed to determine the amounts or proportions of the target or signal. A detection is "qualitative" when it refers to, relates to, or involves identification of a quality or kind of the target or signal in terms of relative abundance to another target or signal, which is not quantified.

The term "signal", as used herein, refers to a detectable output associated with a particular target of interest and can be used to qualitatively or quantitatively detect the target. In particular, exemplary signals can include, for example, presence of positive or negative electrical charges, propensity to form positive or negative electrical charges, mass-to-charge ratios, and others identifiable to a skilled person.

The term "sample" as used herein indicates a limited quantity of something that is indicative of a larger quantity of that something, including but not limited to solids and/or fluids from a biological environment, specimen, cultures, tissues, or portions thereof. In some embodiments, the sample can be an aqueous or organic solution containing a particular substance of interest. Exemplary samples in the sense of the current disclosure include an environment sample collected from water, soil, air or the outer space, samples collected from a surface of a facility, equipment or system, food or pharmaceutical preparation, including, for example, blood, urine, drinking water, agricultural irrigation water and others identifiable to a skilled person upon a reading of the present disclosure.

In particular, in some embodiments, the sample is an unprepared sample. The term "unprepared sample" as used herein refers to a sample that has not been subjected to sample preparation, wherein the term "sample preparation" refers to the way a sample is treated prior to its analysis to introduce an azide ($-N_3$) group or alkyne group into a molecule (e.g., by incorporating an azide- or alkyne-bearing sugar or amino acid into a biomolecule; see, e.g. [Ref 2-5]) for binding to a detection reagent through "click chemistry" as described herein, and other sample preparations that would be apparent to a skilled person upon a reading of the present disclosure. In particular, in some instances absence of sample preparation in the sense of the present disclosure can result in a method wherein reacting an azide presenting molecule with the alkyne presenting molecule is performed without any information beforehand as to the quantity, concentration, or chemical reactivity of the compound presenting the alkyne group, and possibly also the chemical composition of the medium when the reaction is expected to occur.

Accordingly, according to some embodiments of the disclosure, the amount of azide or alkyne in a molecule to be detected, and thus the amount of molecule to be detected (e.g. an alkyne-presenting molecule) is not known beforehand in the unprepared samples herein described.

In particular, in some embodiments, the selective detection of alkyne-presenting molecules, and in particular 17α-ethinylestradiol, comprises: contacting the detection reagent with the unprepared sample for a time and under a condition so as to bind the one or more alkyne-presenting molecules possibly present in the sample to the detection reagent wherein the detection reagent comprises an organic or organometallic label moiety presenting an azide or sulfonyl azide group and wherein binding of the azide or sulfonyl azide group to the alkyne-presenting molecules results in emission of a signal from the organic or organometallic label moiety.

In embodiments in which the alkyne is a terminal alkyne, detection according to embodiments herein described can be performed by contacting the unprepared sample with a label organic moiety presenting an azide group to allow reaction of the alkyne group with the azide group through click chemistry. In some of those embodiments, the reaction can be performed as herein described at room temperature or up to temperatures of between approximately 40-60° C. or of up to temperatures of 100° C. A skilled person can choose the temperature by considering, for example, the thermal stability of the label organic moiety presenting an azide group (e.g. if the label organic moiety presenting an azide group is an aryl azide, the temperature can be kept below 60° C. or other temperature suitable to prevent thermal decomposition of the label organic moiety presenting an azide). In particular, in those embodiments in which the alkyne is an internal alkyne and the temperature is to be maintained below approximately 60° C., a catalysts such as a ruthenium-based catalyst (e.g., Cp*RuCl(PPh$_3$)$_2$) can be used in place of Cu(I) to perform the reaction (see, e.g., [Ref 6]). In addition, in those embodiments in which the alkyne is a terminal alkyne, the amount of Cu(I) as herein described can be 5-20 mol % relative to the alkyne component or up to 50 mol % or up to stoichiometric amounts. In addition, in those embodiments in which the alkyne is a terminal alkyne, the amount of ascorbic acid used as herein described can be in excess amounts. In particular, in those embodiments in which the alkyne is a terminal alkyne, the reaction is expected to allow detection of alkyne presenting molecule at least nanomolar levels and possibly picomolar levels.

In embodiments in which the alkyne is an internal alkyne, detection according to embodiments herein described can be performed by contacting alkyne presenting molecule with a label organic moiety presenting an azide group to allow reaction of the alkyne group with the azide group to perform click chemistry. In some of those embodiments, the reaction can be performed at to temperatures of between approximately 40-60° C. or of up to temperatures of 100° C. or higher. A skilled person can choose the temperature by considering, for example, the thermal stability of the label organic moiety presenting an azide group (e.g. if the label organic moiety presenting an azide group is an aryl azide, the temperature can be kept below 60° C. or other temperature suitable to prevent thermal decomposition of the label organic moiety presenting an azide; or if the label organic moiety presenting an azide group is an alkyl azide, the temperature can be above 100° C. and in particular at a temperature above 100° C. suitable to prevent thermal decomposition of the label organic moiety presenting an azide). In particular, in those embodiments in which the alkyne is an internal alkyne and the temperature is to be maintained below approximately 60° C., a catalysts such as a ruthenium-based catalyst (e.g., Cp*RuCl(PPh$_3$)$_2$) can be used in place of Cu(I) to perform the reaction (see, e.g., [Ref 6]). In addition, in those embodiments in which the alkyne is an internal alkyne, the amount of Cu(I) as herein described can be 5-20 mol % relative to the alkyne component or up to 50 mol % or up to stoichiometric amounts. In addition, in those embodiments in which the alkyne is an internal alkyne, the amount of ascorbic acid used as herein described can be in excess amounts. In particular, in those embodiments in which the alkyne is an internal alkyne, the reaction is expected to allow detection of alkyne presenting molecule at least nanomolar levels and possibly picomolar levels.

The term "label", as in "label organic moiety" or "label organometallic moiety", as used herein as component of an organic molecule or organometallic complex refers to a moiety capable of detection, including but not limited to radioactive isotopes, fluorophores, chemiluminescent dyes, chromophores, enzymes, enzymes substrates, enzyme cofactors, enzyme inhibitors, dyes, organometallic complexes, and the like that are identifiable by a skilled person.

In some embodiments, the detection reagent adapted to selectively bind to one or more alkyne-presenting molecules possibly present in the sample is adapted to comprise one or more azide functional groups. In particular, in some embodiments, the azide can bind to a terminal alkyne present on another alkyne-presenting molecule (e.g., 17α-ethinylestradiol) to form a triazole via a Hüisgen reaction as herein described.

Figure 3:
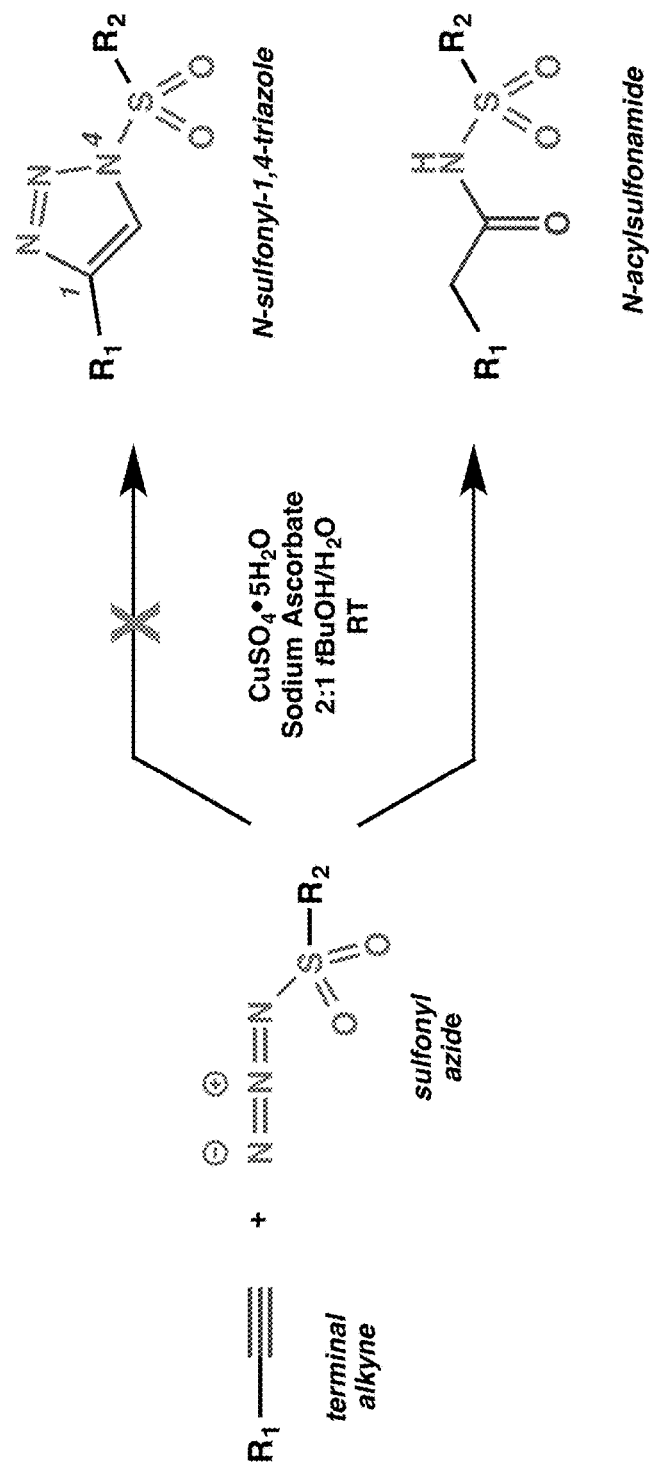
FIG. 3 shows a schematic of an exemplary reaction between terminal alkynes and sulfonyl azides to furnish N-acylsulfonamides according to embodiments herein described.

In other embodiments, the detection reagent adapted to selectively bind to one or more 17α-ethinylestradiol molecules possibly present in the sample is adapted to comprise one or more sulfonyl azide functional groups. In particular, in some embodiments, the sulfonyl azide can bind to a terminal alkyne present on another molecule (e.g. 17α-ethinylestradiol) to form a N-acylsulfonamide (FIG. 3). In contrast to their triazole counterparts, the N-acylsulfonamides that arise from this reaction are not all solids in nature but can be obtained as oils or syrups that are isolated in pure form after column chromatography. It is this characteristic that can make sulfonyl azide-based probes useful for the detection/analysis of EE2 by GC-MS.

In some embodiments, the label organic or organometallic moiety is adapted to produce a signal detectable by mass spectrometry when bound to the one or more alkyne-presenting molecules, and in particular 17α-ethinylestradiol molecules, present in the sample.

In particular, in some embodiments, the label organic or organometallic moiety is adapted to produce a signal detectable by mass spectrometry when the detection reagent is bound to the one or more alkyne-presenting molecules, and in particular 17α-ethinylestradiol molecules, present in the sample by comprising a positively charged moiety. In particular, in some embodiments, the positively charged moiety can comprise a pyridinium moiety.

In particular, in some embodiments, the label organic or organometallic moiety is adapted to produce a signal when the detection reagent is bound to the one or more 17α-ethinylestradiol molecules present in the matrix by comprising a ferrocenyl moiety.

Figure 4:
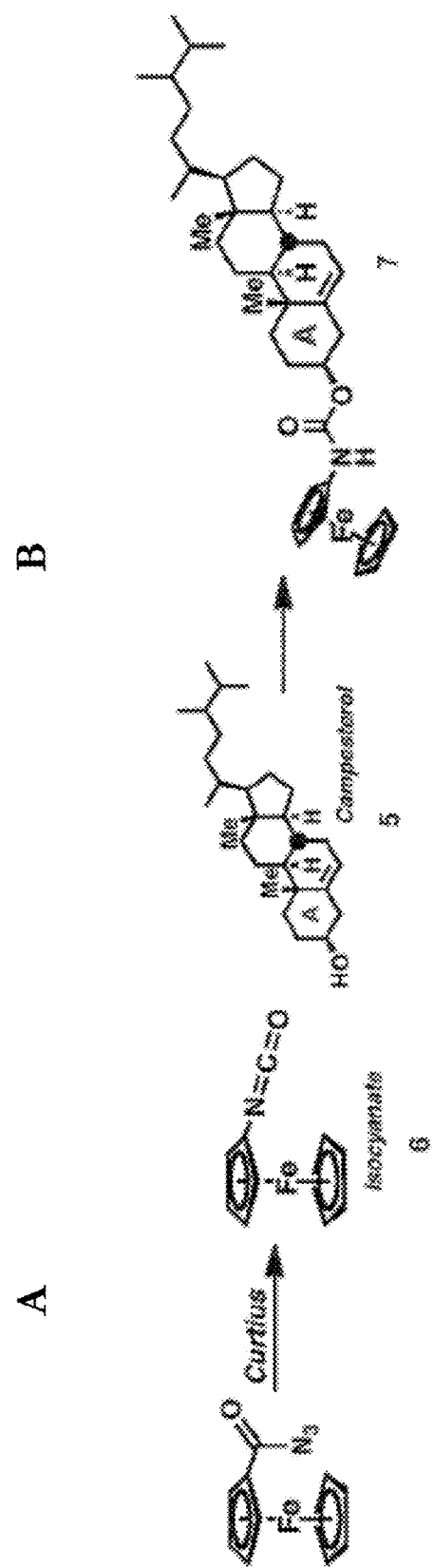
FIG. 4 shows a schematic of reaction to generate a ferrocenyl probe according to embodiments herein described and a reaction between a ferrocenyl probe and a target molecule.
Figure 5:
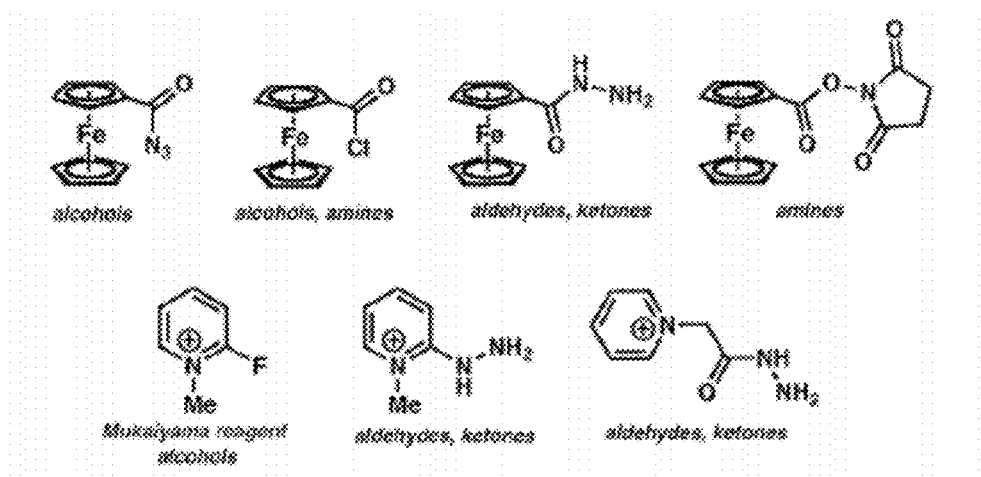
FIG. 5 shows exemplary commonly used ferrocene-based and N-alkyl pyridine-based tags for the LC-MS analysis of steroids and other neutral species. The reactive centers in the analytes of interest that can be labeled are given below the tag's structure. Note that these tags work only for MS methods operating in the (+) ion mode.

In some embodiments, ferrocene-based tags can be used in mass spectrometry to enhance the signals of low-abundance analytes in a mixture in particular in connection with functionalities ionizable by the mass spectrometer to yield in highly stable ferrocenyl radical cations that are readily captured in the detector. In some embodiments, use of such tags allows detection of steroids (including natural and synthetic samples) which are poorly ionizable, neutral species and as such are difficult to detect and analyze by LC-MS if extremely low concentrations of these are encountered in a given mixture. An exemplary reaction including ferrocene tags by reacting the steroid Campesterol (5) (at its hydroxyl group in ring A) with a ferrocenyl isocyanate tag 6 (obtained via a Curtius rearrangement of the acyl azide ferrocene precursor) to furnish adduct 7 which was easily ionizable and thus detected by the mass spectrometer is illustrated in FIG. 4. An additional advantage in using a ferrocene tag is the fact that the signal arising from the modified steroid often experiences a significant enhancement above background. Besides the use of ferrocene tags, other ionizable tags that include N-alkylated pyridinyl probes have become widely used in the mass spectrometry community for the detection of analytes that are present in mixture at sub-nanomolar and even sub-picomolar concentrations (FIG. 5). Once again, these tags use highly reactive centers that efficiently label the steroid nuclei and it is this inherent reactivity that causes other reactive analytes to become "tagged" as well. Therefore, in the end, the researcher still finds himself/herself analyzing a mixture of "tagged" species rather than a few entities.

In particular, in some embodiments, the detection reagent is selected from the group consisting of formulas XV-XVIII:

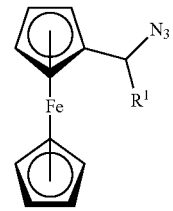

XV

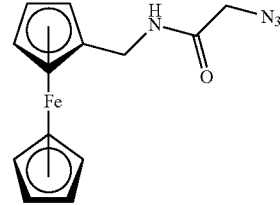

XVI

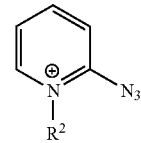

XVII

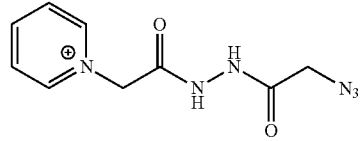

XVIII wherein:

$R^1$ and $R^2$ are independently $C_1$-$C_8$ alkyl.

In particular, in some embodiments, the detection reagent has a structure according to formula XIX:

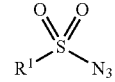

XIX wherein R is $C_1$-$C_8$ alkyl, trifluoromethyl, or substituted or unsubstituted aryl.

In particular, in some embodiments, the detection reagent can be selected from the group consisting of formulas XX-XIV:

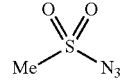

XX

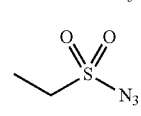

XXI

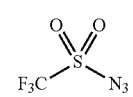

XXII

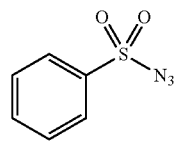

XXIII

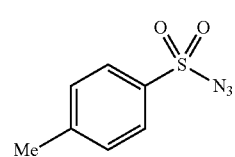

XXIV

In some embodiments, the selective detecting of an alkyne-presenting molecule, and in particular 17α-ethinylestradiol, is achieved by measuring the mas-to-charge ratio of the detection reagent after the contacting.

Figure 2:
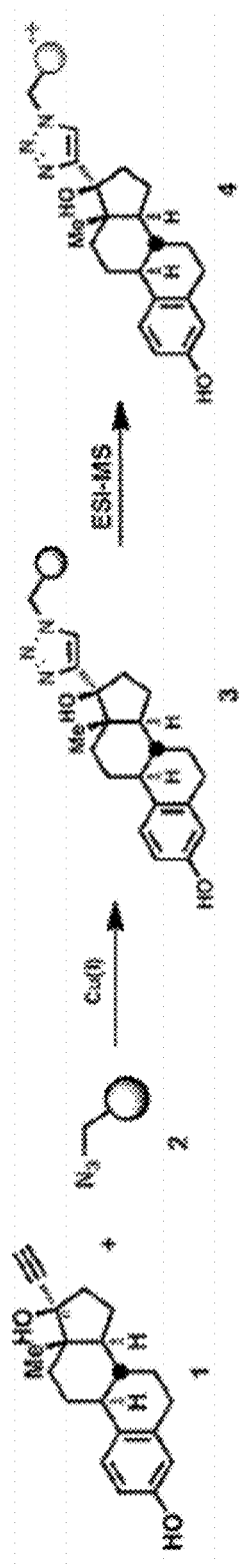
FIG. 2 shows a schematic Structure of the contraceptive 17α-ethinylestradiol and an exemplary reaction with an easily ionizable azide-bearing tag for ESI(+)-MS methodology according to embodiments herein described.

In some embodiments, the selective detecting of 17α-ethinylestradiol is achieved by detecting a positive charge on the detection reagent in a mass spectrometer after the contacting. In particular, in some embodiments, the detection is based on the Copper(I)-catalyzed azide-alkyne 1,3-dipolar cycloaddition reaction, commonly referred to as Click chemistry, with azido-based detection reagents with positively charged, or ionizable to positively charged, signaling moieties. Thus, the initial cycloaddition reaction between EE2 (1) and the azido tag (2) leads to the formation of the tagged adduct 3 which upon undergoing ionization in the MS instrument leads to the formation of stable radical cations (4) easily measurable in the machine (FIG. 2).

In some embodiments, the selective detecting of an alkyne-presenting molecule in a mass spectrometer can also be achieved by coupling of the mass spectrometry detection with fluorescence detection. In some embodiments, the coupling of the mass spectrometry detection with fluorescence detection can be achieved by performing the contacting with detection reagents comprising fluorescent or pre-fluorescent moieties, such as those of U.S. Provisional Application 61/790,019 and U.S. Non-Provisional application Ser. No. 14/201,530 and entitled "Methods for The Selective Detection of Alkyne-Presenting Molecules and Related Compositions and Systems" filed on Mar. 7, 2014, wherein the detection reagents comprising fluorescent or pre-fluorescent moieties further comprise organic or organometallic moiety adapted to produce a signal detectable by mass spectrometry as described herein.

In some embodiments, the detection reagents comprising fluorescent or pre-fluorescent moieties can comprise the organic or organometallic moiety adapted to produce a signal detectable by mass spectrometry by attachment of the organic or organometallic moiety to a substituent on the detection reagents comprising fluorescent or pre-fluorescent moieties. For example, if the detection reagents comprising fluorescent or pre-fluorescent moieties comprises a $C_1$-$C_8$ alkyl substituted with an amine or alcohol, the amine or alcohol can be reacted with a reagent such as the ferrocene acid chloride reagent of FIG. 5 to attach the organometallic moiety adapted to produce a signal detectable by mass spectrometry to the detection reagents comprising fluorescent or pre-fluorescent moieties. Similarly, if for example the detection reagents comprising fluorescent or pre-fluorescent moieties comprises a $C_1$-$C_8$ alkyl substituted with an aldehyde or ketone, the aldehyde or ketone can be reacted with a reagent such as the hydrazinopyridinium compound of FIG. 5 to attach the organic moiety adapted to produce a signal detectable by mass spectrometry to the detection reagents comprising fluorescent or pre-fluorescent moieties.

In some embodiments, the coupling of the mass spectrometry detection with fluorescence detection as described herein can allow the detection of an alkyne-presenting molecule in addition to the identification of the alkyne-presenting molecule. For example, detection of an alkyne-presenting moiety can be achieved by detecting the fluorescence of a detection reagent comprising fluorescent or pre-fluorescent moieties and comprising organic or organometallic moiety adapted to produce a signal detectable by mass spectrometry, and after the detection, the alkyne-presenting molecule can be identified by the mass spectrum produced by the organic or organometallic moiety.

In some embodiments, the selective detecting of an alkyne-presenting molecule in a mass spectrometer can also be coupled with sequestering of the alkyne-presenting molecule. In some embodiments, the coupling of the detecting and sequestering can be performed by contacting the herein described detection reagents comprising fluorescent or pre-fluorescent moieties and organic or organometallic moiety adapted to produce a signal detectable by mass spectrometry, wherein the detection reagents are further attached to a support of a sequestration reagent such as, for example, the sequestration reagents of U.S. Provisional Application 61/790,757 and U.S. Non-Provisional application Ser. No. 14/201,545 and entitled "Methods for The Selective Sequestration of Alkyne-Presenting Molecules and Related Compositions and Systems" filed on Mar. 7, 2014.

In some embodiments, the detection reagents comprising fluorescent or pre-fluorescent moieties and organic or organometallic moiety adapted to produce a signal detectable by mass spectrometry can be attached to the support of the sequestration reagent through functional groups on the substituents on the fluorescent or pre-fluorescent moieties. For example, if the support is a polymeric resin (e.g. such as that used in solid phase peptide synthesis) comprising alcohol groups, then the detection reagents comprising fluorescent or pre-fluorescent moieties and organic or organometallic moiety adapted to produce a signal detectable by mass spectrometry can comprise on the fluorescent or pre-fluorescent moieties, for example, $C_1$-$C_8$ alkyl substituted with a carboxylic acid which can be attached to the alcohol groups of the polymeric resin (for example by converting the carboxylic acid to an acid chloride or by using ester synthesis techniques known to a skilled person) through ester bonds.

In some embodiments, the sequestered alkyne-presenting moieties can be released from the support of the sequestration reagent comprising the attached detection reagents comprising fluorescent or pre-fluorescent moieties and organic or organometallic moieties adapted to produce a signal detectable by mass spectrometry following the sequestration. For example, if the detection reagent is attached to the support of the sequestration reagent through an ester bond as herein described, the alkyne-presenting moiety covalently bound to the detection reagent can be released from the support following the sequestration by hydrolysis of the ester bond. In some embodiments, the sequestration of the alkyne-presenting molecule followed by release of the alkyne-presenting molecule can allow sequestration of an alkyne-presenting molecule followed by detection and/or identification of the alkyne-presenting molecule, for example by analysis of the mass spectrum produced by the organic or organometallic moieties covalently bound to the released alkyne-presenting molecules.

In some embodiments, the systems herein described can be provided in the form of kits of parts. In a kit of parts, one or more detection reagents and copper(I) sources can be comprised in the kit independently. In particular, in some embodiments, the copper(I) source can be a Cu(I) salt (e.g. CuCl or CuBr). In other embodiments, the copper(I) source can be a Cu(II) salt (e.g. CuSO$_4$) that can be combined with a reducing agent (e.g. ascorbic acid) to provide Cu(I) ions. In other embodiments, the copper(II) source can be a mixture of Cu(0) and Cu(II) sources that can react through comproportionation to provide Cu(II) ions. In other embodiments, the kit of parts can further comprise a reducing agent (e.g. ascorbic acid) to prevent oxidation of the Cu(I) source.

In particular, also described herein is a detection reagent for the selective detection of alkyne-presenting molecules, and in particular 17α-ethinylestradiol, by mass spectrometry. In particular, in some embodiments, the detection reagent comprises one or more label organic or organometallic moieties, the label organic or organometallic moieties each presenting an azide or sulfonyl azide group; wherein the label organic or organometallic moieties are adapted to produce a signal when the detection reagent is bound to one or more alkyne-presenting molecules.

The term "signaling moiety" as used herein refers to an atom or group of atoms capable of providing a signal. In particular, in some embodiments, the signaling moiety can be a positively charged moiety such as, for example, a pyridinium moiety. In particular, in other embodiments, the signaling moiety can be a moiety easily ionizable in a mass spectrometer to a positive moiety, such as, for example, a ferrocenyl moiety.

In particular, in some embodiments, the detection reagent has a structure selected from the group consisting of Formulas XXV-XXVIII:

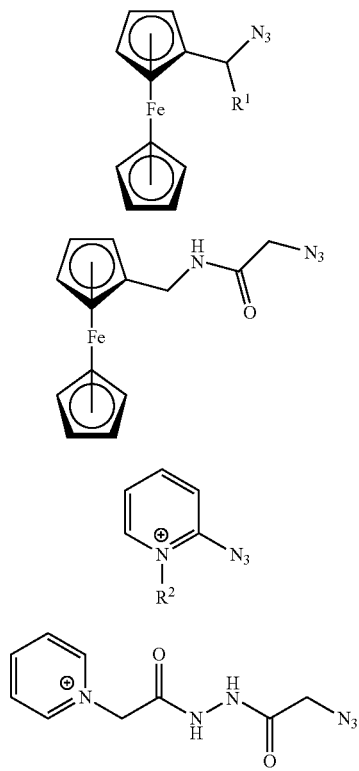

XXV

XXVI

XXVII

XXVIII wherein:
R$^1$ and R$^2$ are independently C$_1$-C$_8$ alkyl.

In particular, in some embodiments, the detection reagent can have a structure according to formula XXIX:

XXIX

In particular, in some embodiments, the detection reagent can be selected from the group consisting of Formulas XXX-XXXIV:

XXX

XXXI

XXXII

XXXIII

XXXIV

In some embodiments, the detection reagents comprising organic or organometallic moiety adapted to produce a signal detectable by mass spectrometry can further be comprised in detection reagents comprising fluorescent or pre-fluorescent moieties, such as those of U.S. Provisional Application 61/790,019 and U.S. Non-Provisional application Ser. No. 14/201,530 and entitled "Methods for The Selective Detection of Alkyne-Presenting Molecules and Related Compositions and Systems" filed on Mar. 7, 2014.

In some embodiments, the comprising of the detection reagents comprising organic or organometallic moiety adapted to produce a signal detectable by mass spectrometry in detection reagents comprising fluorescent or pre-fluorescent moieties can be achieved by attachment of the organic or organometallic moiety to a substituent on the detection reagents comprising fluorescent or pre-fluorescent moieties. For example, if the detection reagents comprising fluorescent or pre-fluorescent moieties comprises a C$_1$-C$_8$ alkyl substituted with an amine or alcohol, the amine or alcohol can be reacted with a reagent such as the ferrocene acid chloride reagent of FIG. 5 to attach the organometallic moiety adapted to produce a signal detectable by mass spectrometry to the detection reagents comprising fluorescent or pre-fluorescent moieties. Similarly, if for example the detection reagents comprising fluorescent or pre-fluorescent moieties comprises a $C_1$-$C_8$ alkyl substituted with an aldehyde or ketone, the aldehyde or ketone can be reacted with a reagent such as the hydrazinopyridinium compound of FIG. 5 to attach the organic moiety adapted to produce a signal detectable by mass spectrometry to the detection reagents comprising fluorescent or pre-fluorescent moieties.

In some embodiments, the detection reagents comprising organic or organometallic moiety adapted to produce a signal detectable by mass spectrometry can further be comprised in sequestration reagents such as, for example, the sequestration reagents of U.S. Provisional Application 61/790,757 and U.S. Non-Provisional application Ser. No. 14/201,545 and entitled "Methods for The Selective Sequestration of Alkyne-Presenting Molecules and Related Compositions and Systems" filed on Mar. 7, 2014.

In some embodiments, the comprising of the detection reagents comprising organic or organometallic moiety adapted to produce a signal detectable by mass spectrometry can further be comprised in sequestration reagents can be achieved by attaching the herein described detection reagents comprising fluorescent or pre-fluorescent moieties and organic or organometallic moiety adapted to produce a signal detectable by mass spectrometry to the support of the sequestration reagent through functional groups on the substituents on the fluorescent or pre-fluorescent moieties. For example, if the support is a polymeric resin (e.g. such as that used in solid phase peptide synthesis) comprising alcohol groups, then the detection reagents comprising fluorescent or pre-fluorescent moieties and organic or organometallic moiety adapted to produce a signal detectable by mass spectrometry can comprise on the fluorescent or pre-fluorescent moieties, for example, $C_1$-$C_8$ alkyl substituted with a carboxylic acid which can be attached to the alcohol groups of the polymeric resin (for example by converting the carboxylic acid to an acid chloride or by using ester synthesis techniques known to a skilled person) through ester bonds.

In some embodiments, the sequestered alkyne-presenting moieties can be released from the support of the sequestration reagent comprising the attached detection reagents comprising fluorescent or pre-fluorescent moieties and organic or organometallic moieties adapted to produce a signal detectable by mass spectrometry following the sequestration. For example, if the detection reagent is attached to the support of the sequestration reagent through an ester bond as herein described, the alkyne-presenting moiety covalently bound to the detection reagent can be released from the support following the sequestration by hydrolysis of the ester bond. In some embodiments, the sequestration of the alkyne-presenting molecule followed by release of the alkyne-presenting molecule can allow sequestration of an alkyne-presenting molecule followed by detection and/or identification of the alkyne-presenting molecule, for example by analysis of the mass spectrum produced by the organic or organometallic moieties covalently bound to the released alkyne-presenting molecules.

Described herein are methods and related compositions and systems that in some embodiments can be used in the selective detection and quantification of steroids, and in particular, the selective detection and quantification of 17α-ethinylestradiol.

Further characteristics of the present disclosure will become more apparent hereinafter from the following detailed disclosure by way or illustration only with reference to an experimental section.

EXAMPLES

The methods for the selective detection, and quantification of 17α-ethinylestradiol and related compositions and systems herein described are further illustrated in the following examples, which are provided by way of illustration and are not intended to be limiting.

Figure 7:
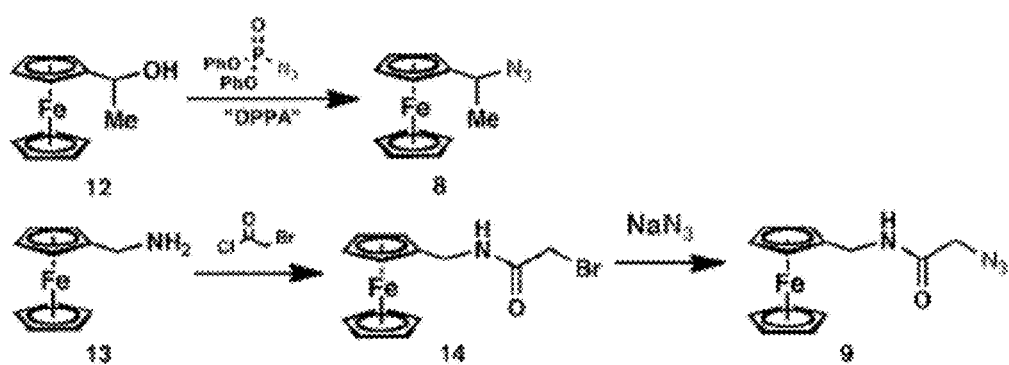
FIG. 7 shows a schematic of an exemplary synthesis of ferrocenyl tags according to embodiments herein described.

Example 1: Synthesis of Ferrocenyl Azides and N-Alkyl Pyridine Azides for EE2 Derivatization, Detection and Signal Enhancement in Liquid Chromatography-Mass Spectrometry The proposed synthesis of an exemplary azide modified ferrocenyl probe is presented in FIG. 7. Thus, the synthesis of ferrocene azide tag 8 can be achieved in one step by treating commercially available ferrocene ethanol (12) with diphenylphosphoroylazide (DPPA) to furnish tag 8 in 94% yield as a bright yellow solid. The synthesis of ferrocene tag 9 starts out by alkylating aminoferrocene 13 with bromoacetyl chloride to give the alkyl bromide intermediate 14. Treatment of 14 with sodium azide is expected to furnish tag 9.

Figure 8:
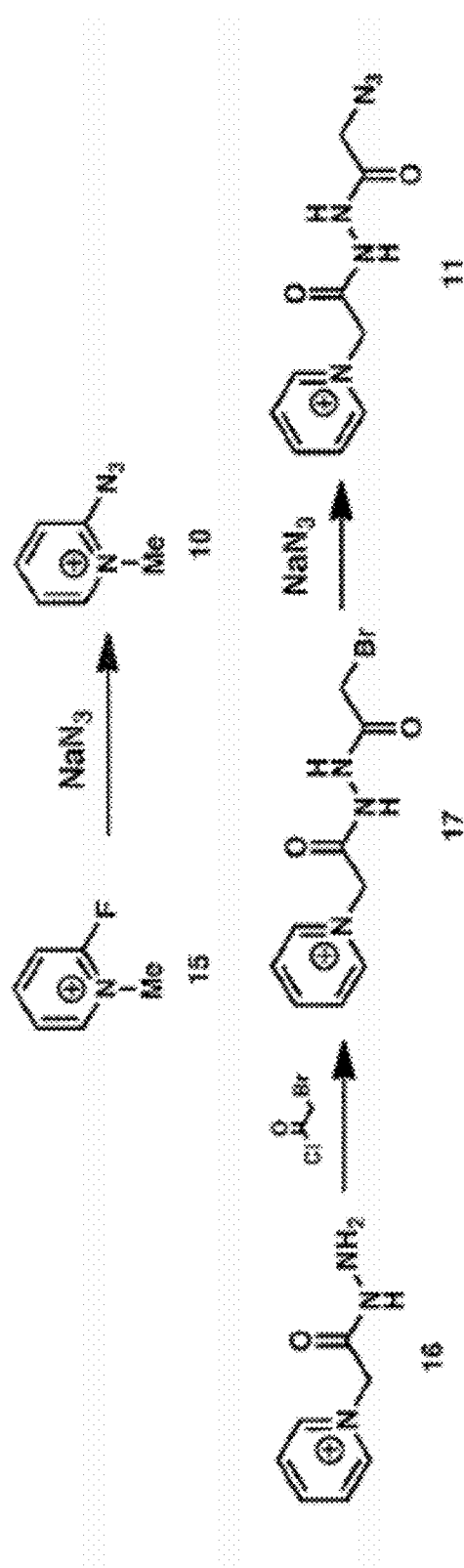
FIG. 8 shows a schematic of exemplary syntheses of N-alkylpyridyl tags according to embodiments herein described.

The synthesis of an exemplary N-alkylpyridinyl probe is shown in FIG. 8. In particular, the synthesis of the N-alkylpyridinyl azide tag 10 is achieved by treating Mukaiyama's pyridine (15) with sodium azide in one step (FIG. 8, top), and the N-alkylpyridine azido tag 11 can be constructed from the acylhydrazine precursor 16 via alkylation with bromoacetyl chloride to give 17. Treatment of 17 with sodium azide is expected to furnish tag 11 (FIG. 8, bottom).

Both ferrocenyl probes and N-alkylpyridinyl probe described above are expected to react in a 1,3-dipolar cycloaddition fashion (Click chemistry) with EE2 to furnish triazole containing adducts that can be easily detected (e.g., with UV-Vis detection) via LC-MS methods. In addition, due to the exceptionally efficient ionization of these tags, a signal enhancement for the EE2 adduct is expected in the MS portion of the analysis. Thus, even if a mixture of analytes is reacted with these tags, only the EE2 will react with them, thus becoming the only species benefiting from such signal enhancement during the mass spectrometry acquisition phase.

Figure 6:
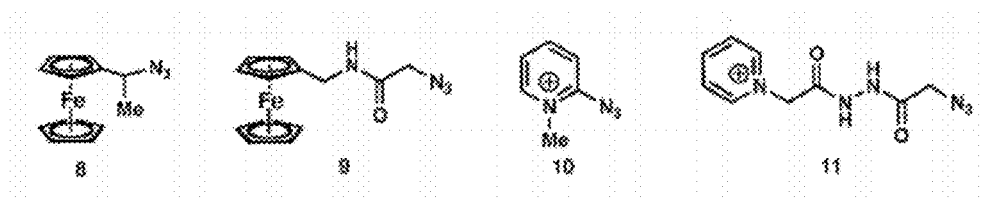
FIG. 6 shows exemplary azide-modified ferrocenyl and N-alkyl pyridinyl tags according to embodiments herein described.

Given that the inherent reactivity of these tags towards many species can create a mixture of "labeled" analytes, in some embodiments a tag that can be used to target only a specific analyte of interest has been synthesized. The synthetic hormone EE2 lends itself as a unique candidate to exploit this selectivity approach. EE2 possesses a terminal alkyne unit that can be used for specific tagging. This alkyne can be reacted with organic azides and sulfonyl azides to yield covalent adducts that can then be further studied using analytical techniques such as LC-MS and GC-MS. In some embodiments, the tagging can be accomplished by way of azide-containing ferrocene and azido N-alkyl pyridine tags (e.g., compounds 8-11 in FIG. 6) for the detection of EE2 in various samples. In some embodiments, the characteristics possessed by these types of tags are: 1) the tags can contain an easily ionizable group, for example, the ferrocenyl and the N-alkyl pyridine units, and 2) their syntheses can be simple and high yielding to procure the materials in usable quantities and in pure form for desired derivatization steps.

Figure 9:
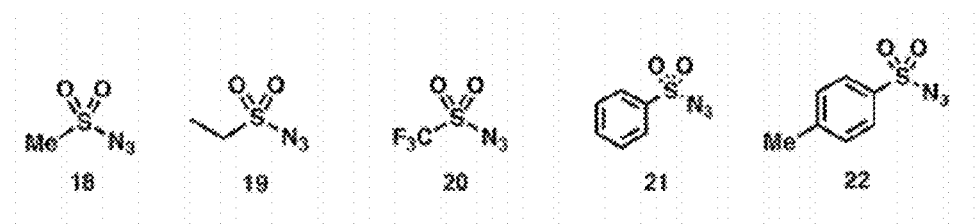
FIG. 9 shows exemplary sulfonyl azides for EE2 tagging and subsequent GC-MS analysis according to embodiments herein described.

Example 2: Synthesis of Sulfonyl Azides for EE2 Derivatization and Detection via Gas Chromatography-Mass Spectrometry Means The use of sulfonyl azides to react with terminal alkynes was discovered in 2006. Applicants expect that the use of this highly orthogonal reaction to specifically label EE2 in a mixture of analytes. An array of sulfonyl azides, differing in the nature of the alkyl group attached to the sulfone moiety is proposed herein for synthesis and screening under click chemistry reaction conditions with EE2 (18-22, FIG. 9).

Figure 10:
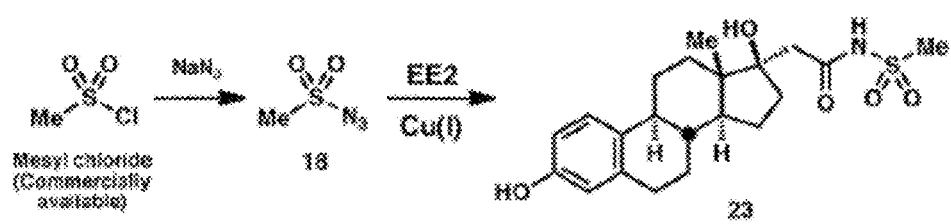
FIG. 10 shows a schematic of an exemplary synthesis of a mesyl azide and its reaction with EE2 to furnish an acylsulfonamide tagged EE2.
Figure 11:
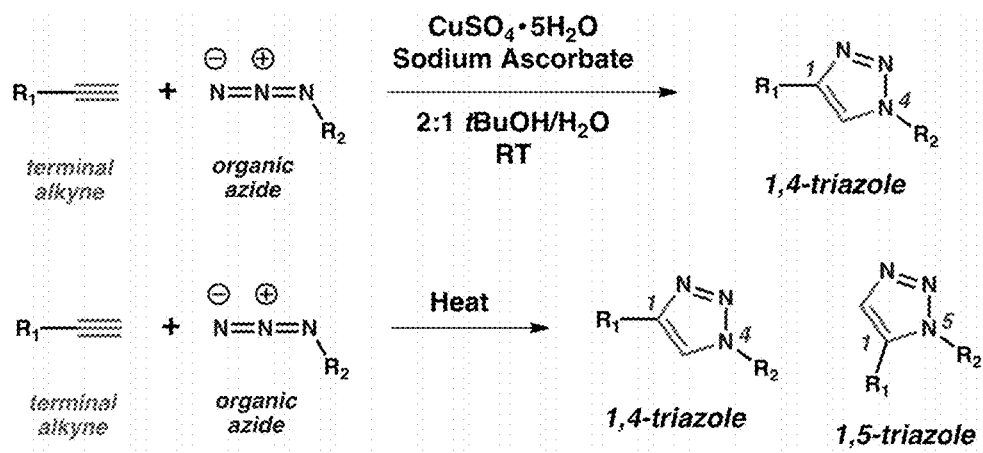
FIG. 11 shows a schematic of the Cu(I)-catalyzed Azide-Alkyne Cycloaddition (CuAAC) reaction to produce a 1,4-substituted triazole ring joining species R1 and R2, whereas the original, thermal addition of the azide and the alkyne yields the 1,5-substituted product in addition to the 1,4-substituted adduct.
Figure 12:
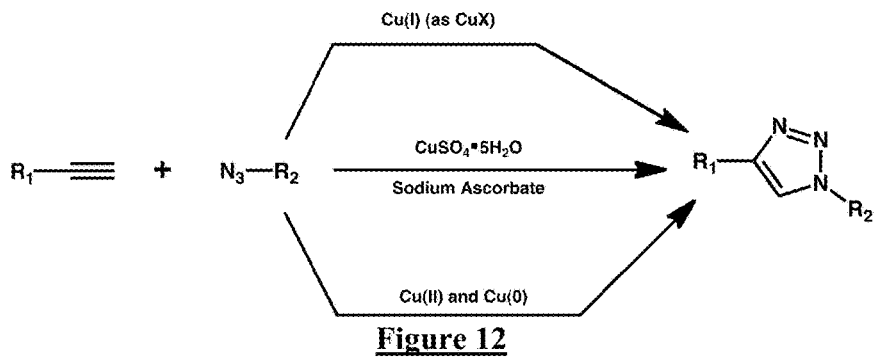
FIG. 12 shows Click chemistry catalyzed by various sources of Cu(I) ions, a) Cu(I) salts; b) Cu(I) from the $CuSO_4$/sodium ascorbate system and c) Cu(I) originating from the Cu(0)/Cu(II) comproportionation reaction as described herein.
Figure 13:
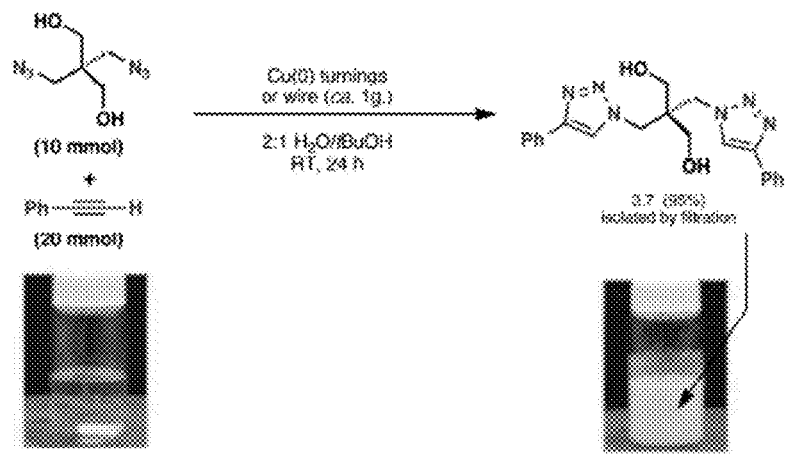
FIG. 13 shows a schematic and image of an exemplary click chemistry reaction using a copper wire as the sole source of catalytic Cu(I) (Fokin group).
Figure 14:
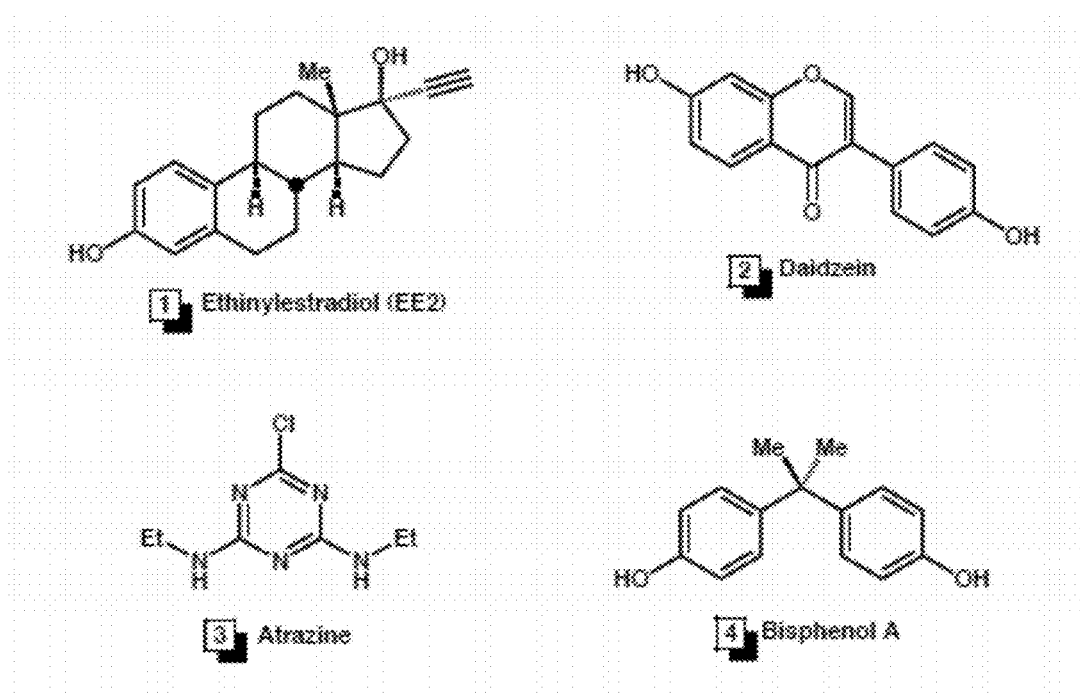
FIG. 14 shows exemplary Endocrine Disrupting Compounds (EDCs).

The rationale behind the use of sulfonyl azides and not other common carbon-based azides in this part of the disclosure is the observation that triazole products arising from the latter species and EE2 were found to be not amenable to GC-MS analysis. This was presumed to be a direct effect of the triazole nucleus present in the adduct which imparts a significant degree of stability and thus a much lower chance of volatilization in the GC injection port. Thus, Applicants expect that using a sulfonyl azide to tag EE2 by forming an N-acylsulfonamide link instead of a triazole unit, this product would possess enough volatility to be detected and quantified by GC-MS. The synthesis of the simplest sulfonyl azide, methylsulfonyl azide 18 and its reaction with EE2 to furnish adduct 23 is presented below in FIG. 10. The rest of the sulfonyl azides can be prepared in a similar fashion starting from the commercially available sulfonyl chlorides.

In summary, the described Example details the syntheses of azide containing tags for the specific detection and analysis of the xenobiotic drug EE2 in water and organic matrices. The tags can be used to specifically label EE2 via click chemistry and once this step has been achieved, quantification of the hormone can be accomplished using LC-MS and GC-MS. The nature of the tags is different for each analytical method employed. Thus, ferrocenyl- and N-alkylpyridinyl-containing azide tags have been proposed for use in LC-MS methods, while sulfonyl azide tags have been designed for their application in GC-MS methodology.

The examples set forth above are provided to give those of ordinary skill in the art a complete disclosure and description of how to make and use the embodiments of the methods for the selective detection of alkyne-presenting molecules and related compositions and systems of the disclosure, and are not intended to limit the scope of what the Applicants regard as their disclosure. Modifications of the above-described modes for carrying out the disclosure can be used by persons of skill in the art, and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Unless otherwise indicated, the term "alkyl" as used herein refers to a linear, branched, or cyclic saturated hydrocarbon group typically although not necessarily containing 1 to about 15 carbon atoms, or 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 15 carbon atoms. The term "cycloalkyl" intends a cyclic alkyl group, typically having 4 to 8, or 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

Unless otherwise indicated, the term "hydrocarbyl" as used herein refers to any univalent radical, derived from a hydrocarbon, such as, for example, methyl or phenyl. The term "hydrocarbylene" refers to divalent groups formed by removing two hydrogen atoms from a hydrocarbon, the free valencies of which may or may not be engaged in a double bond, typically but not necessarily containing 1 to 20 carbon atoms, in particular 1 to 12 carbon atoms and more particularly 1 to 6 carbon atoms which includes but is not limited to linear cyclic, branched, saturated and unsaturated species, such as alkylene, alkenylene alkynylene and divalent aryl groups, e.g., 1,3-phenylene, —CH2CH2CH2-propane-1,3-diyl, —CH2-methylene, —CH═CH—CH═CH—. The term "hydrocarbyl" as used herein refers to univalent groups formed by removing a hydrogen atom from a hydrocarbon, typically but not necessarily containing 1 to 20 carbon atoms, in particular 1 to 12 carbon atoms and more particularly 1 to 6 carbon atoms, including but not limited to linear cyclic, branched, saturated and unsaturated species, such as univalent alkyl, alkenyl, alkynyl and aryl groups e.g. ethyl and phenyl groups.

Unless otherwise indicated, the term "heteroatom-containing" as in a "heteroatom-containing alky group" refers to a alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, and others known to a skilled person, and examples of heteroatom-containing alicyclic groups are pyrrolidino, morpholino, piperazino, piperidino, and other known to a skilled person.

Unless otherwise indicated, the term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

Unless otherwise indicated, the term "alkylamino" as used herein intends an alkyl group bound through a single terminal amine linkage; that is, an "alkylamino" may be represented as —NH— alkyl where alkyl is as defined above. A "lower alkylamino" intends a alkylamino group containing 1 to 6 carbon atoms. The term "dialkylamino" as used herein intends two identical or different bound through a common amine linkage; that is, a "dialkylamino" may be represented as —N(alkyl)2 where alkyl is as defined above. A "lower dialkylamino" intends a alkylamino wherein each alkyl group contains 1 to 6 carbon atoms. Analogously, "alkenylamino", "lower alkenylamino", "alkynylamino", and "lower alkynylamino" respectively refer to an alkenyl, lower alkenyl, alkynyl and lower alkynyl bound through a single terminal amine linkage; and "dialkenylamino", "lower dialkenylamino", "dialkynylamino", "lower dialkynylamino" respectively refer to two identical alkenyl, lower alkenyl, alkynyl and lower alkynyl bound through a common amine linkage. Similarly, "alkenylalkynylamino", "alkenylalkylamino", and "alkynylalkylamino" respectively refer to alkenyl and alkynyl, alkenyl and alkyl, and alkynyl and alkyl groups bound through a common amine linkage.

Unless otherwise indicated, the term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 24 carbon atoms, or aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

Unless otherwise indicated, the term "arene", as used herein, refers to an aromatic ring or multiple aromatic rings that are fused together. Exemplary arenes include, for example, benzene, naphthalene, anthracene, and the like. The term "heteroarene", as used herein, refers to an arene in which one or more of the carbon atoms has been replaced by a heteroatom (e.g. O, N, or S). Exemplary heteroarenes include, for example, indole, benzimidazole, thiophene, benzthiazole, and the like. The terms "substituted arene" and "substituted heteroarene", as used herein, refer to arene and heteroarene molecules in which one or more of the carbons and/or heteroatoms are substituted with substituent groups.

Unless otherwise indicated, the terms "cyclic", "cyclo-", and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

Unless otherwise indicated, the terms "halo", "halogen", and "halide" are used in the conventional sense to refer to a chloro, bromo, fluoro or iodo substituent or ligand.

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents.

Examples of such substituents can include, without limitation: functional groups such as halo, hydroxyl, sulfhydryl, C1-C24 alkoxy, C2-C24 alkenyloxy, C2-C24 alkynyloxy, C5-C24 aryloxy, C6-C24 aralkyloxy, C6-C24 alkaryloxy, acyl (including C2-C24 alkylcarbonyl (—CO-alkyl) and C6-C24 arylcarbonyl (—CO-aryl)), acyloxy (—O-acyl, including C2-C24 alkylcarbonyloxy (—O—CO-alkyl) and C6-C24 arylcarbonyloxy (—O—CO-aryl)), C2-C24 alkoxycarbonyl (—(CO)—O-alkyl), C6-C24 aryloxycarbonyl (—(CO)—O-aryl), halocarbonyl (—CO)—X where X is halo), C2-C24 alkylcarbonato (—O—(CO)—O-alkyl), C6-C24 arylcarbonato (—O—(CO)—O-aryl), carboxy (—COOH), carboxylato (COO$^-$), carbamoyl (—(CO)—NH2), mono-(C1-C24 alkyl)-substituted carbamoyl (—(CO)—NH(C1-C24 alkyl)), di-(C1-C24 alkyl)-substituted carbamoyl (—(CO)—N(C1-C24 alkyl)2), mono-(C5-C24 aryl)-substituted carbamoyl (—(CO)—NH-aryl), di-(C5-C24 aryl)-substituted carbamoyl (—(CO)—N(C5-C24 aryl)2), di-N—(C1-C24 alkyl),N—(C5-C24 aryl)-substituted carbamoyl, thiocarbamoyl (—(CS)—NH2), mono-(C1-C24 alkyl)-substituted thiocarbamoyl (—(CO)—NH (C1-C24 alkyl)), di-(C1-C24 alkyl)-substituted thiocarbamoyl (—(CO)—N(C1-C24 alkyl)2), mono-(C5-C24 aryl)-substituted thiocarbamoyl (—(CO)—NH-aryl), di-(C5-C24 aryl)-substituted thiocarbamoyl (—(CO)—N (C5-C24 aryl)2), di-N—(C1-C24 alkyl),N—(C5-C24 aryl)-substituted thiocarbamoyl, carbamido (—NH—(CO)—NH2), cyano(-C≡N), cyanato (—O—C≡N), thiocyanato formyl (—(CO)—H), thioformyl ((CS)—H), amino (—NH2), mono-(C1-C24 alkyl)-substituted amino, di-(C1-C24 alkyl)-substituted amino, mono-(C5-C24 aryl)-substituted amino, di-(C5-C24 aryl)-substituted amino, C2-C24 alkylamido (—NH—(CO)-alkyl), C6-C24 arylamido (—NH—(CO)-aryl), imino (—CR=NH where R=hydrogen, C1-C24 alkyl, C5-C24 aryl, C6-C24 alkaryl, C6-C24 aralkyl, and others known to a skilled person), C2-C20 alkylimino (CR=N(alkyl), where R=hydrogen, C1-C24 alkyl, C5-C24 aryl, C6-C24 alkaryl, C6-C24 aralkyl, and others known to a skilled person), arylimino (—CR=N(aryl), where R=hydrogen, C1-C20 alkyl, C5-C24 aryl, C6-C24 alkaryl, C6-C24 aralkyl, and others known to a skilled person), nitro (—NO2), nitroso (—NO), sulfo (—SO2-OH), sulfonato (—SO2-O$^-$), C1-C24 alkylsulfanyl (—S-alkyl; also termed "alkylthio"), C5-C24 arylsulfanyl (—S-aryl; also termed "arylthio"), C1-C24 alkylsulfinyl (—(SO)-alkyl), C5-C24 arylsulfinyl (—(SO)-aryl), C1-C24 alkylsulfonyl (—SO2-alkyl), C5-C24 arylsulfonyl (—SO2-aryl), boryl (—BH2), borono (—B(OH)2), boronato (—B(OR)2 where R is alkyl or other hydrocarbyl), phosphono (—P(O)(OH)2), phosphonato (—P(O)(O$^-$)2), phosphinato (—P(O)(O$^-$), phospho (—PO2), phosphino (—PH2), silyl (—SiR3 wherein R is hydrogen or hydrocarbyl), and silyloxy (—O-silyl); and the hydrocarbyl moieties C1-C24 alkyl (e.g. C1-C12 alkyl and C1-C6 alkyl), C2-C24 alkenyl (e.g. C2-C12 alkenyl and C2-C6 alkenyl), C2-C24 alkynyl (e.g. C2-C12 alkynyl and C2-C6 alkynyl), C5-C24 aryl (e.g. C5-C14 aryl), C6-C24 alkaryl (e.g. C6-C16 alkaryl), and C6-C24 aralkyl (e.g. C6-C16 aralkyl).

Unless otherwise indicated, the term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

Unless otherwise indicated, the term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Van Berkel, G. J., et al., "Derivatization for electrospray ionization mass spectrometry. 3. Electrochemically ionizable derivatives." *Anal Chem* 1998 70(8): 1544-1554.
2. Sletten, E. M., et al., "Bioorthogonal chemistry: fishing for selectivity in a sea of functionality." *Angew Chem Int Ed Engl* 2009 48(38): 6974-6998.
3. Prescher, J. A., et al., "Chemical remodelling of cell surfaces in living animals." *Nature* 2004 430(7002): 873-877.
4. Sawa, M., et al., "Glycoproteomic probes for fluorescent imaging of fucosylated glycans in vivo." *Proc Natl Acad Sci USA* 2006 103(33): 12371-12376.
5. Baskin, J. M., et al., "Copper-free click chemistry for dynamic in vivo imaging." *Proc Natl Acad Sci USA* 2007 104(43): 16793-16797.
6. Zhang, L., et al., "Ruthenium-catalyzed cycloaddition of alkynes and organic azides." *J Am Chem Soc* 2005 127 (46): 15998-15999.

The invention claimed is:

1. A method for selectively detecting an alkyne-presenting molecule in an untreated sample, the method comprising:
    contacting the untreated sample with a detection reagent comprising an organic or organometallic label moiety presenting an azide or sulfonyl azide group;
    the contacting performed for a time and under a condition for click chemistry to allow binding of the azide or sulfonyl azide group with one or more alkyne-presenting molecules possibly present in the untreated sample;
    the contacting further performed in absence of a treatment of the untreated sample that introduces the one or more alkyne-presenting molecules into the untreated sample prior to the contacting;
    wherein the binding of the azide or sulfonyl azide group to the alkyne-presenting molecules results in emission of a signal from the organic or organometallic label moiety; and detecting the signal from the organic or organometallic label moiety.

2. The method of claim 1, wherein the sample is an aqueous or organic solution.

3. The method of claim 1, wherein the organic or organometallic label moiety comprises a positively charged moiety.

4. The method of claim 1, wherein the organic or organometallic label moiety comprises a ferrocenyl moiety.

5. The method of claim 1, wherein the detection reagent is selected from the group consisting of formulas XV-XVIII:

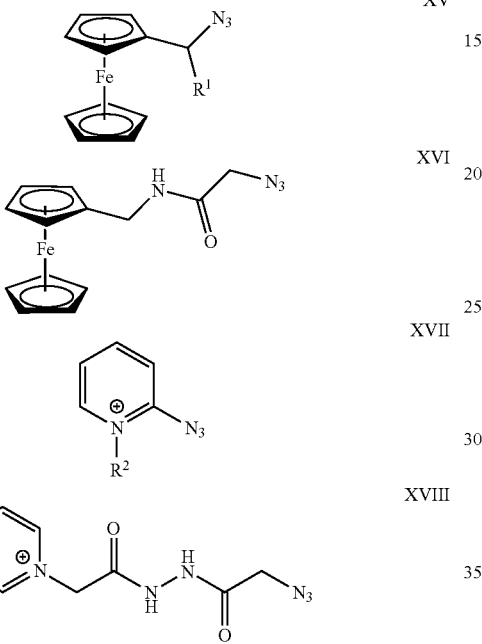

wherein:
$R^1$ and $R^2$ are independently $C_1$-$C_8$ alkyl.

6. The method of claim 1, wherein the detection reagent has a structure according to formula XIX:

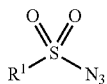

wherein R is $C_1$-$C_8$ alkyl, trifluoromethyl, or substituted or unsubstituted aryl.

7. The method of claim 1, wherein the detection reagent is selected from the group consisting of Formulas XX-XIV:

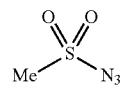

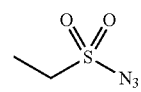

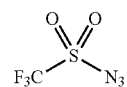

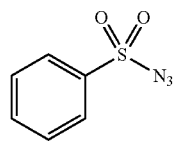

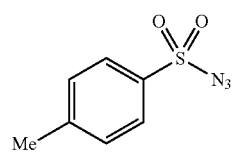

8. The method of claim 1, wherein the detecting is achieved by detecting a positive charge on the detection reagent in a mass spectrometer after the contacting.

9. The method of claim 1, wherein the untreated sample is selected from a solid and/or fluid from a biological environment, specimen, cultures, tissues, or portions thereof.

10. The method of claim 1, wherein the detecting the signal from the organic or organometallic label moiety comprises mass spectrometry.

* * * * *